United States Patent [19]

Semm et al.

[11] Patent Number: 4,909,782

[45] Date of Patent: Mar. 20, 1990

[54] TISSUE PUNCH

[75] Inventors: Horst K. Semm, Munich; Peter Neumann, Furth, both of Fed. Rep. of Germany

[73] Assignee: Wisap-Gesellschaft Fur Wissenschaftlichen Apparatebau mbH, Sauerlach, Fed. Rep. of Germany

[21] Appl. No.: 346,306

[22] Filed: May 2, 1989

Related U.S. Application Data

[63] Continuation of Ser. No. 93,582, Sep. 4, 1987, abandoned.

[30] Foreign Application Priority Data

Sep. 4, 1986 [DE] Fed. Rep. of Germany ....... 3630203

[51] Int. Cl.⁴ .............................................. A61B 17/32
[52] U.S. Cl. .................................................... 606/171
[58] Field of Search ...................... 128/305, 752–755; 604/22

[56] References Cited

U.S. PATENT DOCUMENTS

| | | | |
|---|---|---|---|
| 4,324,243 | 4/1982 | Helfgott et al. | 604/22 |
| 4,428,748 | 1/1984 | Peyman et al. | 604/22 |
| 4,516,398 | 5/1985 | Wuckinich | 604/22 |
| 4,589,414 | 5/1986 | Yoshida et al. | 604/22 X |

FOREIGN PATENT DOCUMENTS 2018601 10/1979 United Kingdom .................. 604/22

Primary Examiner—Michael H. Thaler
Attorney, Agent, or Firm—Fleit, Jacobson, Cohn, Price, Holman & Stern

[57] ABSTRACT

A tissue punch for removing tissue parts from the human or animal body is described, which comprises the actual operating instrument, as well as a separate driving unit, which is connected by means of a flexible force transmission member to the operating instrument. The operating instrument comprises a surgeon-guided outer tube and an inner tube slidably arranged therein having a cutting edge for separating the tissue parts. The inner tube is also supplied with a vacuum by means of a hose connection for removing a separated tissue part from said inner tube. The operation of the inner tube or the cutting edge connected thereto, as well as the suction are controlled by a separate control unit.

6 Claims, 1 Drawing Sheet

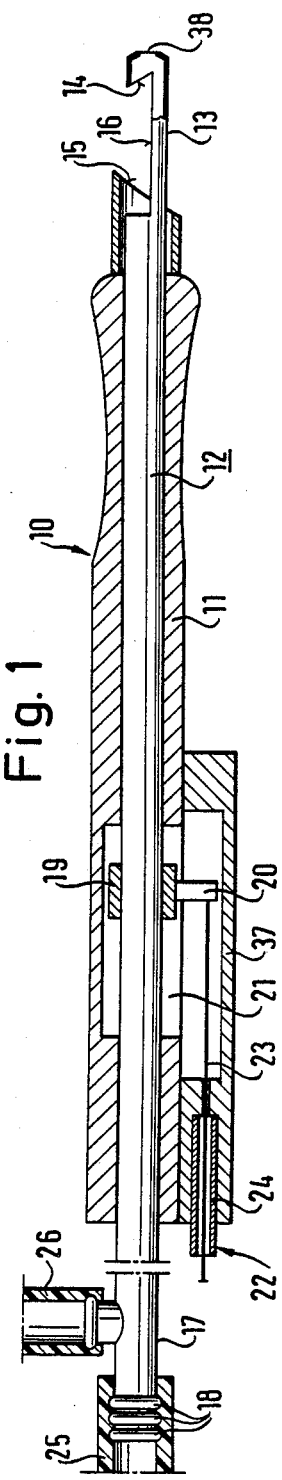
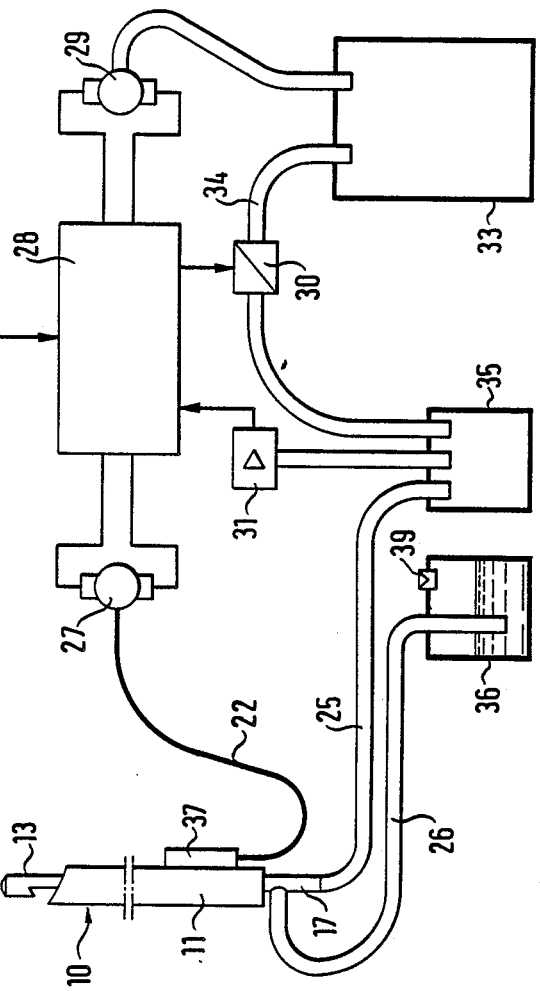

TISSUE PUNCH

This application is a continuation of application Ser. No. 093,582, filed Sept. 4, 1987, now abandoned.

The invention relates to a tissue punch for removing tissue parts from the human or animal body, having a fixed outer tube, with a part having a cutting edge movably arranged on the opening of the outer tube for separating a tissue part and for transferring the separated tissue part into the interior of the tube and with an actuator for the movable part.

Such tissue punches, which can also be called tissue morcellators, are used in intra-abdominal, pelviscopic or endoscopic surgery for removing tissue parts. The latter can e.g. be tumors, myomas or even organs. The tissue punch is introduced with the aid of a trocar cannula into the stomach region, where the tissue is cut off as carefully as possible whilst being visually monitored.

The known tissue punches are operated by means of a hand lever, which is fitted to the outer tube serving as the guide tube. In the inoperative state, the part provided with the cutting edge is under spring loading at a given distance from the opening of the guide tube, which is also provided with a cutting edge. Thus, the tissue punch can be brought into a position in which the tissue part to be separated is located between the two cutting edges. The surgeon then presses together the hand levers contrary to spring tension and due to the resulting shearing effect the tissue part is separated and simultaneously moved into the interior of the guide tube. This process can be repeated until a reception zone located in the interior of the guide tube is filled with tissue parts. The tissue punch must then be completely removed from the body and emptied.

Such manually operated tissue punches suffer from the disadvantage that actuation requires a considerable force, which fatigues the surgeon. For various reasons such a tissue punch is designed in such a way that only small tissue parts can be separated. Therefore if a larger tissue volume has to be removed, the surgeon very frequently has to perform the fatiguing hand movement for operating the tissue punch. The repeated removal of the tissue punch from the trocar cannula for emptying purposes is also disadvantageous and must take place after every five punching processes.

The problem of the present invention is to provide a tissue punch of the aforementioned type, which avoids the frequent emptying processes and aims at preventing fatigue on the part of the surgeon.

According to the invention this problem is solved in that the actuator comprises a separate driving unit controllable by means of a switch and a flexible force transmission means between the driving unit and the movable part.

Thus, the invention is based on the idea of separately constructing the operating instrument and the actuator and also providing a high power drive. This has the advantage that the operating instrument can be more easily handled and that the operator no longer has to perform the strength-sapping and fatiguing operation. It is merely necessary to operate a switch and the latter initiates the cutting movement of the operating instrument. The flexible force transmission means ensures a substantially random association between the driving unit and the operating instrument.

According to a preferred further development of the invention, the reception zone can be supplied via a hose liner with a vacuum for the purpose of emptying said zone. This measure has the advantage that a random number of tissue portions can be removed, without having to remove the tissue punch for this purpose from the stomach area. This considerably reduces the operating period.

It can be particularly advantageous to connect the hose line to a tissue collecting container, which can be suddenly placed under vacuum with the aid of a control means.

According to another advantageous development of the invention, the tube and the movable part are fitted in one another in airtight manner when the tissue punch is in the closed state and at the free end of the movable part is provided an air inlet. This air inlet and the remaining seal mean that the overpressure prevailing outside the tissue punch can be made to act on the tissue part for obtaining an optimum suction action.

It is advantageous for the transport of the tissue parts to supply a lubricant by means of a further hose line. The lubricant can prevent drying out of the hose line and an increase of friction.

The lubricant supply is made particularly simple in that the further hose line is connected to a lubricant storage tank in such a way that when the hose connection is subject to vacuum action, lubricant is sucked into the hose connection. A physiological saline solution is e.g. suitable as the lubricant.

According to a further preferred development of the invention, the driving unit comprises an electric motor. It is also preferable for the switch for operating the driving unit to be constructed as a foot-operated switch. This allows the surgeon to use both hands for guiding and manipulating the operating instrument at the operating point.

It has proved to be very reliable when the flexible transmission means comprises a flexible shaft, which is located in a flexible guide sleeve.

The invention is also advantageously constructed in such a way that a control means is provided, which is at least connected to the driving unit and to a vacuum production device and that the control means following a tripping of the foot-operated switch, firstly controls the driving unit for actuating the movable part of the tissue punch and then the device for producing the vacuum. Thus, when the operating instrument has been brought into the desired position, through an effortless operation of the switch, it is automatically possible to initiate the shearing process and the suction of the separated tissue part, without having to divert the attention of the surgeon for this purpose.

The device for producing the vacuum preferably comprises connecting to a vacuum supply container a vacuum pump controlled by the control means. Said container is connected by a valve controlled by the control means to the tissue collecting container, whose pressure is monitored by means of a sensor and evaluated by the control means.

The movable part of the tissue punch comprises an inner tube slidably mounted in the outer tube and which completely traverses the latter, being provided at its front end with the cutting edge and at its rear end with a hose connection and which is connected to the force transmission means.

The invention is described in greater detail hereinafter relative to an embodiment and the attached drawings, wherein show:

FIG. 1 Diagrammatically a longitudinal section through the tissue punch part serving as an operating instrument.

FIG. 2 Diagrammatically further functional units of the tissue punch.

FIG. 1 shows in longitudinal section the operating instrument 10 of the tissue punch. It comprises a fixed outer tube 11, which is held and guided by the surgeon, and an inner tube 12 longitudinally displaceably arranged in outer tube 11 and which constitutes the movable part of the operating instrument. The inner tube 12 is provided at its front end 13 with a laterally open cavity 16, which is bounded by a cutting edge 14 directed towards the outer tube 11. Opposite to the cutting edge 14 is provided in the extension of outer tube 11 a cutting edge counter part 15. If the cutting edge 14 is moved past the cutting edge counter part 15 through a movement of inner tube 12, the two parts act in the manner of a punch or shear.

The rear end 17 of inner tube 12 is led out of the outer tube 11 and in the presently represented embodiment is provided with serrations 18 for mounting a suction hose 25. In place of serrations 18, rear end 17 of inner tube 12 can also be provided with another device suitable for connecting a hose.

In order to operate the movable part, i.e. the inner tube 12 of the operating instrument 10, on said inner tube is fitted a ring 19, which is provided with a dog 20. Dog 20 is led out of the outer tube 11 via an elongated slot 21 and is connected to a cable means 22, comprising a movable shaft 23 and a guide sleeve 24 fixed in a rearward boring of the casing part 37 and surrounding the inner movable shaft 23. Guide sleeve 24 is supported on a casing part 37, which covers the elongated slot 21 to the outside, without impeding a longitudinal movement of dog 20 in slot 21. A longitudinal movement of shaft 23 is transferred by means of dog 20 and ring 19 to the inner tube 12.

FIG. 1 illustrates the basic position of the operating instrument, in which the front part 13 of inner tube 12 is extended from outer tube 11, so that the cutting edge 14 and counting edge counterpart 15 face one another at a predetermined distance. If in this position the operating position is brought with cavity 16 up to a tissue and then the cable means 22 is operated, then inner tube 12 is drawn into outer tube 11 and as a result of the shearing effect of cutting edge 14 and cutting edge counterpart 15, the particular tissue is sheared. Simultaneously through the displacement of inner tube 12, cavity 16 is covered and tightly sealed by the cutting edge counter part or by the outer tube 11.

With respect to FIG. 2, a description will now be given of how, in this position of inner tube 12 and with the aid of a suddenly occurring vacuum, with which the inner tube 12 is sucked over the suction hose 25, a separated tissue part is removed from the operating instrument 10. In order that the suction action can take place, on the front face of the front end 13 of inner tube 12 is provided an air inlet 38.

FIG. 2 diagrammatically shows the operating instrument 10 in its basic position. By means of the cable means 22, the suction hose 25 and a feed hose 26, operating instrument 10 is connected in freely movable manner with control, actuating, supply and disposal means, which can be fixed. If it would appear desirable, it is obviously also possible to arrange said means on a support, which when necessary can be brought into the most appropriate position.

The cable means 22 is connected by means of a not shown gear to a driving unit 27, which can be preferably constructed as an electric motor. All movements are controlled by means of a control unit 28, which can be equipped with pneumatic, electropneumatic, electrohydraulic or electronic control means. To control unit 28 are also connected a vacuum pump 29, a solenoid valve 30, a vacuum sensor 31 and a foot-operated switch 32.

A vacuum storage tank 33 is subject to the action of the vacuum pump 29 and is connected by a vacuum line 34 controlled by solenoid valve 30 to a tissue collecting container 35. The pressure of the tissue collecting container 35 is monitored by control unit 28 by means of vacuum sensor 31. Suction hose 25 also issues into the tissue collecting container 35.

Feed hose 26 constitutes the connection between a lubricating fluid container 36 and the operating instrument-side end of the suction duct, which is formed by the inner tube 12 and the hose 25. The instrument-side opening of feed hose 26 is not illustrated in detail in FIG. 1. However, it can be easily gathered from the hereinafter described function of the feed hose 26 that the latter is preferably connected to inner tube 12 prior to the connection of suction hose 25.

The function of the tissue punch will now be described in detail relative to FIGS. 1 and 2. If control unit 28 is switched on, operating instrument 10 is brought into the basic position shown in FIG. 1, which is also adopted on releasing switch 32 or in the case of a fault. If the foot-operated switch 32 is now operated, the operating instrument closes and, if it is held against tissue, shears off a certain amount of tissue. As soon as the operating instrument is in its "closed" position, i.e. when cavity 16 is covered, the suction phase starts. The solenoid valve 30 is controlled by the control unit 28, so that a vacuum is suddenly applied to the tissue collecting container 35 by means of the vacuum storage tank 33. As a result, the tissue part in cavity 16 is sucked by means of the suction hose 25 into the tissue collecting container 35. Simultaneously lubricant is sucked out of container 36 by means of the feed hose 26 and supplied to the suction hose 25, so that the tissue transfer hose does not dry out and the tissue slides up to the tissue collecting container 35 without sticking. The suction hose 25 can, under these conditions, be up to 2 m long. As a result of a corresponding cross-sectional dimensioning of feed hose 26, a dosing of the lubricant can take place. A quantity control can also take place by a pressure valve 39 on container 36.

It is possible to check by means of the vacuum sensor 31 connected to the tissue collecting container 35, whether the tissue part has entered the container, because in the suction hose 25 the tissue part acts as a plug, which closes the suction hose 25 for as long as it is located in the latter. As soon as a corresponding pressure rise is recorded in the tissue collecting container 35, the suction process is considered to be ended and the operating instrument 10 is returned by control unit 28 to its basic position. The opening speed of the operating instrument 10 is much higher than the closing speed.

In the case of a permanent operation of the foot-operated switch 32, the cycle of the operating instrument 10 "open - close - suck" is repeated. When the switch is no longer operated, the operating instrument returns to its basic position and is not moved again. Thus, tissue of random volume can be easily removed during an endoscopic operation. This tissue is conveyed portionwise in the tissue collecting container and thereby removed from the interior of the body and the operating instrument can remain permanently in the latter. The physical operating activity of the surgeon is limited to the guidance of the operating instrument 10 and to the operation of switch 32. As in the known manual morcellator, the operating process can be performed under direct visual control in known manner.

The described tissue punch can be varied in that a manually operated switch is provided in place of the foot-operated switch 32. It is also possible to operate drive unit 27 pneumatically, electropneumatically or hydraulically-pneumatically instead of by means of an electric motor. The force transfer performed by the cable means 22 to the operating instrument 10 can also be effected by means of a hydraulically or pneumatically operating device.

We claim:

1. A tissue punch for intra-abdominal, pelviscopic or endoscopic surgery, said tissue punch comprising:
    an outer tube serving as a handpiece,
    an inner tube
    having a front end with lateral opening,
    a cutting edge bounding said lateral opening, and
    a reception cavity connected to said lateral opeing for receiving sheared tissue,
    said inner tube being slidably arranged in an axial direction in said outer tube, and
    actuator means for driving said inner tube between a retracted position and an extended position,
    said outer tube having a counter-part for said cutting edge of said inner tube,
    said cutting edge and said counter-part acting together for shearing tissue when said inner tube is driven from said extended position to said retracted position,
    suction means for producing a suction pressure in said inner tube in said retracted position, said suction means being connected to said inner tube,
    control unit means and control switching means for controlling said actuator means and said suction means, and
    tissue collecting means for collecting sheared tissue, said tissue collecting means being connected to said inner tube and to said suction means,
    an air inlet located at said front end of said inner tube and connected to said reception cavity to provide an inlet for air to be sucked into said inner tube by said suction means when said inner tube is in said retracted position, and
    lubrication feed means being connected to a rearward end of said inner tube upstream from the connection of said suction means to said inner tube for supplying a lubricant into said inner tube in front of sheared tissue when a suction pressure is applied to said inner tube for aiding in moving sheared tissue into said tissue collecting means from said inner tube.

2. A tissue punch according to claim 1, wherein said outer tube covers said lateral opening in an airtight manner when said inner tube is driven to said retracted position.

3. A tissue punch according to claim 1, wherein said suction means includes a vacuum pump controlled by said control unit means and connected to a vacuum storage tank, said vacuum storage tank being connected by means of a valve controlled by said control unit means to said tissue collecting means, and the pressure in said tissue collecting means being monitored by a vacuum sensor.

4. A tissue punch according to claim 1, wherein the rearward end of said inner tube is connected to said tissue collecting means by a suction hose and said lubrication feed means includes a feed hose connected to a lubricant storage tank.

5. A tissue punch according to claim 4, wherein said lubricant storage tank includes a valve means for controlling a quantity of lubricant supplied into said inner tube.

6. A tissue punch according to claim 1, wherein said control switching means is a foot-operated switch.

* * * * *